United States Patent [19]

Lewis et al.

[11] Patent Number: 5,328,927
[45] Date of Patent: Jul. 12, 1994

[54] HETERCYCLIC COMPOUNDS, PROCESSES FOR THEIR PREPARATION AND PHARMACEUTICAL COMPOSITIONS CONTAINING THEM

[75] Inventors: Richard T. Lewis, Harlow; Kevin J. Merchant; Angus M. MacLeod, both of Bishops Stortford, all of United Kingdom

[73] Assignee: Merck Sharpe & Dohme, Ltd., Hertfordshire, England

[21] Appl. No.: 21,826

[22] Filed: Feb. 24, 1993

[30] Foreign Application Priority Data

Mar. 3, 1992 [GB] United Kingdom ............ 9204577.2
Mar. 31, 1992 [GB] United Kingdom ............ 9207053.1
May 27, 1992 [GB] United Kingdom ............ 9211192.1

[51] Int. Cl.$^5$ .................. A61K 31/405; A61K 31/34; C07D 209/16; C07D 209/10
[52] U.S. Cl. ............................... 514/415; 514/443; 514/469; 514/470; 548/504; 548/507; 549/467; 549/466; 549/214; 549/4; 549/49; 549/58; 549/51; 549/52; 549/53; 549/55; 549/56
[58] Field of Search ............ 548/504, 507; 514/415, 514/469, 470, 443; 549/467, 214, 466, 49, 58, 4, 51, 52, 53, 55, 56

[56] References Cited

U.S. PATENT DOCUMENTS

| | | | |
|---|---|---|---|
| 2,517,826 | 8/1950 | Avakian et al. ............ | 260/329 |
| 4,390,526 | 6/1983 | Gorecki et al. ............ | 424/177 |
| 4,501,733 | 2/1985 | Horig et al. ............ | 514/17 |
| 4,663,349 | 5/1987 | Repta ............ | 514/535 |
| 4,665,157 | 5/1987 | Wright ............ | 530/328 |
| 4,680,283 | 7/1987 | Veber et al. ............ | 514/17 |

FOREIGN PATENT DOCUMENTS 0134578  3/1985  European Pat. Off. ......... 548/316.4
(List continued on next page.)

OTHER PUBLICATIONS

Encyclopedia of Chemical Technology, vol. 2, Antibiotics (Survey) (1978), p. 809.
(List continued on next page.)

Primary Examiner—Mary C. Lee
Assistant Examiner—Joseph K. McKane
Attorney, Agent, or Firm—Robert J. North; Melvin Winokur

[57] ABSTRACT

Compounds of formula (I), and salts and prodrugs thereof

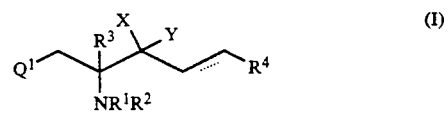

wherein
$Q^1$ is halo substituted phenyl; naphthyl; indolyl; benzthiophenyl; benzofuranyl; benzyl; or fluorenyl;
... is an optional covalent bond;
one of X and Y is H and the other is hydroxy or $C_{1-6}$alkoxy, or X and Y are together =O or =NOR$^5$;
$R^1$ and $R^2$ are H; $C_{1-6}$alkyl optionally substituted by hydroxy, cyano, COR$^c$, CO$_2$R$^c$, CONR$^c$R$^d$, or NR$^c$R$^d$ (where R$^c$ and R$^d$ are H, $C_{1-6}$alkyl or phenyl($C_{0-4}$alkyl) optionally substituted by $C_{1-6}$alkyl, $C_{1-6}$alkoxy, halo and trifluoromethyl); phenyl($C_{1-4}$alkyl) (optionally substituted by $C_{1-6}$alkyl, $C_{1-6}$alkoxy, halo or trifluoromethyl); COR$^c$; CO$_2$R$^c$; CONR$^c$R$^d$; COC$_{1-6}$alkylNR$^c$R$^d$; CONR$^c$COOR$^d$; or SO$_2$R$^c$;
$R^3$ is H, $C_{1-6}$alkyl or $C_{2-6}$alkenyl; and
$R^4$ is phenyl optionally substituted by $C_{1-6}$alkyl, $C_{2-6}$alkenyl, $C_{2-6}$alkynyl, halo, cyano, nitro, trifluoromethyl, trimethylsilyl, OR$^a$, SR$^a$, SOR$^a$, NR$^a$R$^b$, NR$^a$COR$^b$, NR$^a$CO$_2$R$^b$, CO$_2$R$^a$ or CONR$^a$R$^b$, where R$^a$ and R$^b$ are H, $C_{1-6}$alkyl, phenyl or trifluoromethyl; are tachykinin antagonists.

13 Claims, No Drawings

FOREIGN PATENT DOCUMENTS

| | | | |
|---|---|---|---|
| 0230151A3 | 7/1987 | European Pat. Off. | 548/469 |
| 0333174A3 | 9/1989 | European Pat. Off. | 544/106 |
| 394989A2 | 10/1990 | European Pat. Off. | 548/491 |
| 0394989A3 | 10/1990 | European Pat. Off. | 548/504 |
| 0444132A1 | 8/1991 | European Pat. Off. | 548/542 |
| 1906322 | 9/1969 | Fed. Rep. of Germany | 548/469 |
| 2528069 | 6/1974 | Fed. Rep. of Germany | 548/504 |
| 2054588A | 2/1981 | United Kingdom | 546/290 |

OTHER PUBLICATIONS

Molecular Pharmacology, vol. 29, pp. 34–38 (1986), by M. A. Cascieri, et al., entitled "Conformationally Constrained Tachykinin Analogs Which Are Selective Ligands for the Eledoisin Binding Site".

Peptide Hormones, Jun. 1976, pp. 1–7, by J. Rudinger, entitled "Characteristics of the amino acids as components of a peptide hormone sequence".

Biol. Chem. Hoppe-Seyler, vol. 369, pp. 1307–1315, Dec. 1988, by S. Stoev, et al.

Tetrahedron Letters, vol. 30, No. 43, pp. 5941–5944, 1989, by R. Jackson, et al.

J. Org. Chem., 1990, vol. 55, pp. 6000–6017, by D. Boger et al.

Bulletin of the Chem. Society of Japan, vol. 40, No. 3, 1967, by S. Sakakibara, et al.

Biochemistry, vol. 24(8) pp. 1813–2100, 1985, by T. Tanaka, et al.

J. of Natural Sciences & Math., vol. 24, No. 1, pp. 69–74, Apr. 1984, by Z. Malik, et al.

Chem. Abstracts, vol. 83, No. 3, Jul. 21, 1975.

Chem. Abstracts, vol. 60, No. 9, Apr. 27, 1964.

Tetrahedron, vol. 47, No. 26, pp. 4763–4774, 1991, by G. Bourne, et al.

Chem. Abstracts, vol. 94, No. 17, Apr. 27, 1981.

Biochem. Pharmacology, vol. 30, No. 21, pp. 3016–3019 Nov. 1, 1981, by K. Fehske, et al.

Chem. Abstracts, vol. 56, No. 8, Apr. 16, 1962.

J. of Pharmacy & Pharmacology, vol. 39, No. 10, Oct. 1987, pp. 809–818, by D. Cooper et al.

J. of Steroid Biochemistry, vol. 16, pp. 503–507, 1982, by M. Baker, et al.

Cancer Research, vol. 42, No. 6, pp. 2115–2120, Jun. 1982, by C. Kwong, et al.

Chem. Abstracts, vol. 56, No. 8, Apr. 16, 1962.

J. Auton. Pharmacol. vol. 13, pp. 23–93, by C. Maggi, et al., 1993.

HETERCYCLIC COMPOUNDS, PROCESSES FOR THEIR PREPARATION AND PHARMACEUTICAL COMPOSITIONS CONTAINING THEM

This invention relates to a class of heterocyclic compounds which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:Arg-Pro-Lys-Pro-Gln-Gln-Phe-Phe-Gly-Leu-Met-$NH_2$

Neurokinin A:His-Lys-Thr-Asp-Ser-Phe-Val-Gly-Leu-Met-$NH_2$

Neurokinin B:Asp-Met-His-Asp-Phe-Phe-Val-Gly-Leu-Met-$NH_2$

Substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13-34 (published by Pitman) and Otsuka and Yanagisawa, "Does Substance P Act as a Pain Transmitter?" TIPS (Dec. 1987) 8 506-510], specifically in the transmission of pain in migraine (B. E. B. Sandberg et al, J. Med Chem, (1982) 25 1009; S. L. Shepeard et al., Br. J. Pharmacol. (1993), 108, 11-12) and in arthritis [Levine et al in Science (1984) 226 547-549]. These peptides have also been implicated in gastrointestinal (GI) disorders and diseases of the GI tract such as inflammatory bowel disease [Mantyh et al in Neuroscience (1988) 25 (3) 817-37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 November 1989 and Grönblad et al "Neuropeptides in Synovium of Patients with Rheumatoid Arthritis and Osteoarthritis" in J. Rheumatol. (1988) 15(12) 1807-10]. Therefore, substance P is believed to be involved in the inflammatory response in diseases such as rheumatoid arthritis and osteoarthritis [O'Byrne et al in Arthritis and Rheumatism (1990) 33 1023-8]. Other disease areas where tachykinin antagonists are believed to be useful are allergic conditions [Hamelet et al Can. J. Pharmacol. Physiol. (1988) 66 1361-7], immunoregulation [Lotz et al Science (1988) 241 1218-21 and Kimball et al, J. Immunol. (1988) 141 (10) 3564-9], vasodilation, bronchospasm, reflex or neuronal control of the viscera [Mantyh et al, PNAS (1988) 85 3235-9] and, possibly by arresting or slowing β-amyloid-mediated neurodegenerative changes [Yankner et al, Science (1990) 250, 279-82], in senile dementia of the Alzheimer type, Alzheimer's disease and Down's Syndrome. Substance P may also play a role in demyelinating diseases such as multiple sclerosis and amyotrophic lateral sclerosis [J. Luber-Narod et. al., poster presented at C.I.N.P. XVIIIth Congress, 28th June-2nd July, 1992].

Peptide tachykinin antagonists containing an indolyl moiety are disclosed in European patent application no. 0 394 989.

In view of their metabolic instability, peptide derivatives are likely to be of limited utility as therapeutic agents. It is for this reason that non-peptide tachykinin receptor antagonists are sought.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

The present invention provides a compound of formula (I), or a salt or prodrug thereof:

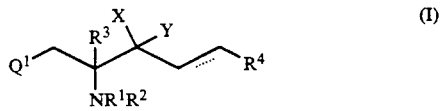

wherein $Q^1$ represents a phenyl group substituted by one or more halo; optionally substituted naphthyl; optionally substituted indolyl; optionally substituted benzthiophenyl; optionally substituted benzofuranyl; optionally substituted benzyl; or optionally substituted fluorenyl;

the dotted line represents an optional covalent bond;

one of X and Y represents H and the other represents hydroxy or $C_{1-6}$alkoxy, or X and Y together form a group =O or =$NOR^5$ where $R^5$ is H or $C_{1-6}$alkyl;

$R^1$ and $R^2$ each independently represent H; $C_{1-6}$alkyl optionally substituted by hydroxy, cyano, $COR^c$, $CO_2R^c$, $CONR^cR^d$, or $NR^cR^d$ (where $R^c$ and $R^d$ each independently represent H, $C_{1-6}$alkyl or phenyl($C_{0-4}$alkyl) optionally substituted in the phenyl ring by one or more of $C_{1-6}$alkyl, $C_{1-6}$alkoxy, halo and trifluoromethyl); phenyl($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $COC_{1-6}$alkyl$NR^cR^d$; $CONR^cCOOR^d$; or $SO_2R^c$; where $R^c$ and $R^d$ are as above defined;

$R^3$ represents H, $C_{1-6}$alkyl or $C_{2-6}$alkenyl; and $R^4$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl.

For the avoidance of doubt, when the covalent bond represented by the dotted line is present, the compounds of formula (I) contain an olefinic double bond.

As used herein, the definition of each expression, when it occurs more than once in any structure, is intended to be independent of its definition elsewhere in the same structure.

Unless otherwise stated the alkyl, alkenyl and alkynyl groups referred to with respect to any of the formulae herein may represent straight, branched or cyclic groups or combinations thereof. Thus, for example, suitable alkyl groups include methyl, ethyl, n- or isopropyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Where $Q^1$ represents optionally substituted fluorenyl, the group is linked through the bridgehead carbon atom, that is to say, C-9 of the fluorenyl moiety.

Where $Q^1$ represents optionally substituted naphthyl, indolyl, benzothiophenyl, benzofuranyl, benzyl or fluorenyl, suitable substituents include $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^a COR^b$, $NR^aCOOR^b$, $COOR^a$ or $CONR^aR^b$, where $R^a$ and $R^b$ are as above defined. One or more substituents may be present and each may be located at any available ring position, except, where $Q^1$ is optionally substituted indolyl, the nitrogen atom. Where $Q^1$ is optionally substituted indolyl, suitable nitrogen substituents include $C_{1-6}$alkyl, optionally substituted phenyl($C_{1-4}$alkyl), $COOR^a$ or $CONR^aR^b$, wherein $R^a$ and $R^b$ are as above defined.

Suitable values of the group $Q^1$ include 3,4-dichlorophenyl, 3-indolyl, 2-naphthyl, 3-naphthyl, 9-fluorenyl, benzyl, 3-benzothiophenyl and 3-benzofuranyl.

Preferably $Q^1$ is 3-indolyl, 3-benzothiophenyl or 3,4-dichlorophenyl, more preferably 3-indolyl.

Preferably the double bond is absent.

Suitably one of X and Y represents hydroxy or $C_{1-6}$alkoxy, such as methoxy, or X and Y together represent =O or =NOH. Preferably one of X and Y represents methoxy, or X and Y together represent =O. More preferably X and Y together represent =O.

Suitable values for $R^1$ and $R^2$ include H, $C_{1-6}$alkyl, $COR^c$, $CO_2R^c$, $CONR^cR^d$ and $COC_{1-6}$alkyl$NR^cR^d$, where $R^c$ and $R^d$ are as previously defined. Preferably $R^1$ and $R^2$ are selected from H, $COR^c$ and $COC_{1-6}$alkyl$NR^cR^d$. More preferably, one of $R^1$ and $R^2$ represents H and the other of $R^1$ and $R^2$ is selected from H, $COR^{13}$ (where $R^{13}$ is $C_{1-6}$alkyl, such as methyl or cyclopropyl, or phenyl($C_{0-3}$alkyl), such as phenyl or phenylpropyl), or $COC_{1-6}$alkyl$N(C_{1-6}$alkyl$)_2$. Particularly preferred are compounds wherein one of $R^1$ and $R^2$ represents H and the other of $R^1$ and $R^2$ represents $CO(CH_2)_nN(CH_3)_2$ where n is 3 or 4.

One subgroup of compounds according to the invention is represented by compounds of formula (I) wherein $R^3$ is H or $C_{1-6}$alkyl.

Preferably $R^3$ represents H or methyl, more preferably H.

Preferably $R^4$ represents substituted phenyl. Suitable phenyl substituents include nitro, trifluoromethyl, trimethylsilyl, bromo, chloro, fluoro, iodo, cyano, methyl, ethyl, cyclopropyl, t-butyl, vinyl, methoxy, phenoxy and amino. Preferably $R^4$ represents disubstituted phenyl, more preferably 3,5-disubstituted phenyl.

Particularly preferred are compounds wherein $R^4$ represents 3,5-bis(trifluoromethyl)phenyl.

One subgroup of compounds according to the invention is represented by compounds of formula (Ia), and salts and prodrugs thereof:

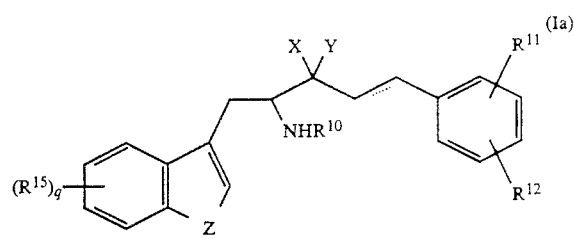

wherein

X and Y are as defined for formula (I);

the dotted line represents an optional covalent bond;

Z represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as previously defined), preferably S or NH;

$R^{10}$ is H, $COR^c$, $CO_2R^c$, $CONR^cR^d$ or $COC_{1-6}$alkyl$NR^cR^d$ (where $R^c$ and $R^d$ are as previously defined), preferably $CO(C_{1-6}$alkyl) or $COC_{1-6}$alkyl$N(C_{1-6}$alkyl$)_2$;

$R^{11}$ and $R^{12}$ each independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined;

each $R^{15}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined; and q is 0, 1, 2 or 3, preferably 0.

A further subgroup of compounds according to the invention is represented by compounds of formula (I) wherein $Q^1$ represents indolyl, benzothiophenyl or dichlorophenyl, preferably 3-indolyl, 3-benzothiophenyl or 3,4-dichlorophenyl; $R^1$ and $R^2$ are selected from H, $C_{1-6}$alkyl, $COR^c$, $CO_2R^c$ and $COC_{1-6}$alkyl$NR^cR^d$; and $R^4$ is 3,5-bistrifluoromethylphenyl. Preferred are compounds according to this subgroup wherein at least one of $R^1$ and $R^2$ is H.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when both $R^1$ and $R^2$ are other than hydrogen, the nitrogen atom to which they are attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of the present invention are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, including diabetic and chemotherapy-induced neuropathy, and postherpetic and other neuralgias; respiratory diseases, particularly those associated with excess mucus secretion such as chronic obstrucutive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I), or a salt or prodrug thereof, for use in therapy.

The present invention further provides a compound of formula (I) or a salt or prodrug thereof for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound or composition of this invention.

In the treatment of conditions involving actions of tachykinins released physiologically in response to noxious or other stimuli, a suitable dosage level is about 0.001 to 50 mg/kg per day, preferably about 0.005 to 10 mg/kg per day, and especially about 0.005 to 5 mg/kg per day. The compounds may be administered on a regimen of 1 to 4 times per day, preferably once or twice daily.

Compounds of formula (I) wherein X and Y together represent =O and the double bond is present may be prepared by reaction of an aldehyde of formula $R^4CHO$, wherein $R^4$ is as defined for formula (I) above, with a compound of formula (II):

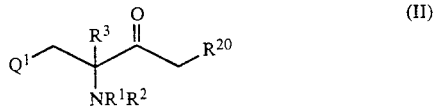

(II)

wherein $Q^1$, $R^1$, $R^2$ and $R^3$ are as defined for formula (I) and $R^{20}$ represents a group $PR^x_3$ or $PO(OR^x)_2$, wherein $R^x$ represents phenyl or $C_{1-10}$alkyl, in the presence of a base.

Suitable bases include alkali metal hydrides, such as, for example, sodium hydride, and strong organic bases such as, for example, 1,8-diazabicylo[5.4.0]undec-7-ene in the presence of anhydrous lithium chloride. Preferred bases include alkali metal carbonates such as potassium carbonate.

The reaction is conveniently effected in a suitable organic solvent, such as an ether, e.g. tetrahydrofuran, suitably at ambient temperature.

The compounds of formula (I) so prepared may be converted to other compounds of formula (I) using standard procedures, as follows. It is to be understood that any suitable combination of the conversion processes described may be employed in order to arrive at the desired compound of formula (I).

Compounds of formula (I) wherein one of X and Y represents H and the other represents hydroxy may be prepared from the corresponding compounds of formula (I) wherein X and Y together represent =O, by reduction.

Suitable reducing agents include, for example, hydride reducing agents such as lithium aluminium hydride and sodium borohydride.

The reaction is conveniently carried out in a suitable organic solvent, such as an ether, e.g. tetrahydrofuran, suitably at ambient temperature.

Compounds of formula (I) wherein one of X and Y represents H and the other represents $C_{1-6}$alkoxy may be prepared from the corresponding compounds of formula (I) wherein one of X and Y represents H and the other represents hydroxy, by alkylation.

Suitable alkylation procedures include treatment of an alcohol of formula (I) with an alkali metal hydride, such as sodium hydride, and a $C_{1-6}$alkylhalide. Suitable halides include, in particular, bromides and iodides.

The reaction is conveniently effected in an anhydrous organic solvent, for example, an ether, e.g. dimethoxyethane, suitably at ambient temperature.

Compounds of formula (I) wherein X and Y together represent =$NOR^5$ may be prepared from the corresponding compounds of formula (I) wherein X and Y together represent =O by the addition of hydroxylamine, or a suitable derivative thereof. Compounds wherein $R^5$ is other than H may be prepared from the corresponding compounds wherein $R^5$ is H by alkylation, for example, using a diazo compound, such as diazomethane, or an alkyl halide or sulphate.

Compounds of formula (I) wherein the double bond is absent may be prepared from the corresponding unsaturated compounds of formula (I) by reduction.

Suitable reduction procedures include catalytic hydrogenation. Suitable hydrogenation catalysts include nobel metals, for example, platinum or palladium, or oxides thereof, which may be supported, for example, on charcoal. A preferred catalyst is Wilkinson's catalyst (tris(triphenylphosphine)rhodium(I)chloride).

The reaction is conveniently effected in a suitable organic solvent, such as an ether, e.g. tetrahydrofuran, an alcohol, e.g. ethanol, or an ester, e.g. ethyl acetate, suitably at ambient temperature.

Compounds of formula (I) may also be prepared from different compounds of formula (I) via other suitable interconversion processes. Interconversion processes are particularly suitable for varying the substituents $R^1$ and $R^2$. For example, compounds of formula (I), wherein one or both of $R^1$ and $R^2$ is/are other than H may be prepared from compounds of formula (I) wherein one or both of $R^1$ and $R^2$ is/are H using conventional methods, such as for example alkylation or acylation. Suitable procedures will be readily apparent to those skilled in the art and are described in the accompanying examples.

Compounds of formula (II) may be prepared from compounds of formula (III)

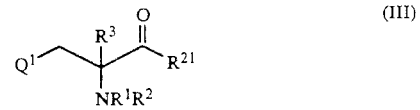

(III)

wherein $Q^1$, $R^1$, $R^2$ and $R^3$ are as defined for formula (I) and $R^{21}$ represents an alkoxy or a suitably substituted amino group, such as a group $NR^yOR^z$, where $R^y$ and $R^z$ represent alkyl, in particular a group $NCH_3(OCH_3)$, by reaction with a compound of formula $CH_3PO(OR^x)_2$, where $R^x$ is an alkyl group, in the presence of a base.

Suitable reaction procedures will be readily apparent to the skilled person and examples thereof are described in the accompanying Examples.

Suitable bases of use in the reaction include alkyl lithiums, such as butyl lithiums.

Compounds of formula (III) are commercially available or may be prepared using standard procedures well known to the skilled person in the art. The compounds of formula (III) are amino acid derivatives. Syntheses of amino acids and derivatives thereof are well documented and are described, for example, in *Chemistry and Biochemistry of the Amino Acids*, ed. G. C. Barrett, Chapman and Hall, 1985.

Where the above-described processes for the preparation of the compounds according to the invention give rise to mixtures of stereoisomers, these isomers may be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following non-limiting Examples illustrate the preparation of compounds according to the invention.

EXAMPLE 1

2-Acetamido-1-(3-benzo[b]thienyl)-5-(3,5-bistrifluoromethylphenyl)-4-penten-3-one a)
2-Acetamido-1-(3-benzo[b]thienyl)-4-diethylphosphono-3-butanone Diethyl methyl phosphonate (13.0 g) was dissolved in dry tetrahydrofuran (200 ml), cooled to −70° C., and treated with 1.6M n-butyl lithium (54 ml), maintaining the internal temperature at below −60° C. The reaction mixture was stirred at −70° C. for 0.5 hours before adding N-acetyl-4-(3-benzo[b]thienyl)-DL-alanine ethyl ester (Int. J. peptide Protein Res., 29, 1987, 118–125) (10.0 g) in dry tetrahydrofuran (100 ml). After stirring for 1.5 hours the reaction was quenched with saturated ammonium chloride. The reaction mixture was extracted with ethyl acetate and washed with water (3×50 ml). The organic phase was dried (MgSO$_4$), filtered and evaporated to yield an oil which was purified on silica using dichloromethane/methanol (95:5) to give the product as an oil (10.6 g).

b)
2-Acetamido-1-(3-benzo[b]thienyl)-5-(3,5-bistrifluoromethylphenyl)-4-penten-3-one A solution of the product of step (a) (10.6 g) in dry tetrahydrofuran (200 ml) was cooled to 0° C., treated with 60% sodium hydride in oil (1.07 g) and stirred for 1 hour. 3,5-Bistrifluoromethyl benzaldehyde (6.5 g) in dry tetrahydrofuran (50 ml) was added dropwise to the reaction mixture which was stirred for 1 hour before quenching with saturated ammonium chloride. The organic layer was separated and the aqueous layer was extracted with ethyl acetate (2×100 ml). The combined organic extracts were washed with water (100 ml), dried (MgSO$_4$), filtered and evaporated. The residue was purified by chromatography on silica using ethyl acetate/petroleum ether (bp 60–80) (2:3) to yield the title compound as a pale yellow solid (10.3 g), mp=172°–173° C.; found: C, 56.15; H, 3:54; N, 2.79; C$_{23}$H$_{17}$F$_6$NO$_2$S.0.25H$_2$O requires C, 56.38; H, 3.60; N, 2.86%.

EXAMPLE 2

2-Acetamido-1-(3-benzo[b]thienyl)-5-(3,5-bistrifluoromethylphenyl)-4-penten-3-ol A solution of the product of Example 1 (2.0 g) was dissolved in ethanol/dichloromethane (5:1, 100 ml) and treated with sodium borohydride (0.156 g). The reaction was stirred for 1 hour and then poured into water (500 ml), extracted with ethyl acetate, dried (MgSO$_4$), filtered, and evaporated to yield an oil which was purified by chromatography on silica using ethyl acetate/petroleum ether (bp 60°–80° C.) to yield the title compound isomer A as a pale yellow solid (0.25 g) mp=190°–191° C.; found: C, 56.19; H, 3.93; N, 2.91; C$_{23}$H$_{19}$F$_6$NO$_2$S.0.25H$_2$O requires C, 56.15; H, 4.00; N, 2.85%.

Further elution yielded the title compound isomer B as a pale yellow solid (0.5 g) mp 94°–95° C., found: C, 56.24; H, 4.01; N, 2.73; C$_{23}$H$_{19}$F$_6$NO$_2$S.0.25H$_2$O requires C, 56.15; H, 4.00; N, 2.85%.

EXAMPLE 3

2-Acetamido-1-(3-benzo[b]thienyl)-5-(3,5-bistrifluoromethylphenyl)-3-methoxy-4-pentene A mixture of the two isomeric alcohols of Example 2 (1.8 g) was dissolved in dry dimethoxyethane (25 ml) and treated with sodium hydride and stirred for 10 minutes before adding iodomethane (0.2 ml). The reaction was stirred for a further 0.5 hours and then quenched with saturated ammonium chloride and extracted with ethyl acetate. The separated organic layer was dried (MgSO$_4$), filtered, and evaporated to yield an oil which was purified by silica chromatography using ethyl acetate/petroleum ether (bp 60°–80° C.), (1:1) to yield the title compound isomer A as a white solid (0.098 g) mp=125°–126° C.; found: C, 57.21; H, 4.33; N, 2.75; C$_{24}$H$_{21}$F$_6$NO$_2$S requires C, 57.48; H, 4.22; N, 2.79%.

Further elution yielded the title compound isomer B as a white solid (0.215 g), mp=164°–165° C.; found: C, 57.10; H, 4.29; N, 2.76; C$_{24}$H$_{21}$F$_6$NO$_2$S requires C, 57.48; H, 4.22; N, 2.79%.

EXAMPLE 4

2-Acetamido-1-(3-benzo[b]thienyl)-5-(3,5-bistrifluoromethylphenyl)-3-pentanone

2-Acetamido-1-(3-benzo[b]thienyl)-5-(3,5-bistrifluoromethylphenyl)-4-penten-3-one (2.0 g) was hydrogenated in tetrahydrofuran (100 ml) using 10% Pd/C (0.5 g) at 50 p.s.i. The product was purified by chromatography on silica using ethyl acetate/petroleum ether (bp 60°–80° C.)(1:1) to yield the title compound as a white solid (1.2 g), mp=83°–84° C.; found: C, 56.41; H, 3.81; N, 2.84; C$_{23}$H$_{19}$F$_6$NO$_2$S requires C, 56.67; H, 3.93; N, 2.87%.

EXAMPLE 5

2-Acetamido-1-(3-benzo[b]thienyl)-5-(3,5-bistrifluoromethylphenyl)-3-pentanol The compound of Example 4 (1.1 g) was treated with sodium borohydride (100 mg) in the same manner as Example 2 to yield the title compound isomer A as a white solid (0.23 g), mp=70°–71° C.; found: C, 56.43; H, 4.22; N, 2.77; $C_{23}H_{21}F_6NO_2S$ requires C, 56.44; H, 4.32; N, 2.86%.

Further elution yielded the title compound isomer B, (0.42 g), mp=113°–114° C.; found: C, 56.27; H, 4.33; N, 2.81; $C_{23}H_{21}F_6NO_2S$ requires C, 56.44; H, 4.32; N, 2.86%.

EXAMPLE 6

2-Acetamido-1-(3-benzo[b]thienyl)-5-(3,5-bistrifluoromethylphenyl)-3-methoxypentane A mixture of the two isomeric alcohols of Example 5 (1.3 g) was treated in the same manner as Example 3 to yield the title compound isomer A, 0.083 g, mp=120°–121° C.; found: C, 56.86; H, 4.27; N, 2.68; $C_{24}H_{23}F_6NO_2S$ requires C, 56.74; H, 4.66; N, 2.76%.

Further elution yielded the title compound isomer B as a white solid (0.075 g), mp=164°–166° C.; found: C, 56.67; H, 4.69; N, 2.81; $C_{24}H_{23}F_6NO_2S$ requires C, 56.74; H, 4.66; N, 2.78%.

EXAMPLE 7

2-Acetamido-5-(3,5-bistrifluoromethylphenyl)-1-(3-indolyl)-4-penten-3-one a) Methyl 2-t-butyloxycarbonylamino-3-(3-(1-t-butyloxycarbonyl)indolyl)propionate L-Tryptophan methyl ester hydrochloride (10 g), was suspended in dichloromethane (200 ml) and triethylamine (3.98 g) was added, followed by di-t-butyl dicarbonate (8.6 g). The reaction was stirred for 1 hour before adding 4-dimethyl aminopyridine (4.8 g) and di-t-butyl dicarbonate (21.4 g). The reaction was stirred for 16 hours and then washed with 10% citric acid (200 ml), water (200 ml), saturated sodium bicarbonate solution (200 ml), water (200 ml) and dried (MgSO4), filtered and evaporated. The residue was purified by chromatography on silica using ethyl acetate/petroleum ether (bp 60°–80° C.) (1:4) to yield the title compound (13.2 g).

b) 2-t-Butyloxycarbonylamino-5-(3,5-bistrifluoromethylphenyl)-1-(3-(1-t-butyloxycarbonyl)indolyl)-4-penten-3-one The title compound was obtained by reaction of the product of part (a) by the method of Example 1.

c) 2-Acetamido-5-(3,5-bistrifluoromethylphenyl)-1-(3-indolyl)-4-penten-3-one The product of part (b) (1.0 g) was dissolved in methanolic hydrogen chloride and stirred for 16 hours. The solvent was removed and the residue was dissolved in pyridine (5 ml) and acetic anhydride (1 ml) was added. The reaction was stirred for 16 hours and then poured onto ice/water. The mixture was extracted with ethyl acetate (2×100 ml) and the organic extract was washed with 10% citric acid (100 ml), brine (100 ml), saturated sodium bicarbonate (100 ml), dried (MgSO4) filtered and evaporated. The residue was purified by column chromatography on silica using isopropanol/petroleum ether (bp 60°–80° C.), (1:9), to yield the title compound as a pale yellow solid (0.35 g), mp=68°–70° C.; found: C, 58.23; H, 4.06; N, 5.55; $C_{23}H_{18}F_6N_2O_2.0.25H_2O$ requires C, 58.42; H, 3.94; N, 5.92%.

EXAMPLE 8

2-Acetamido-5-(3,5-bistrifluoromethylphenyl)-1-(3-indolyl)-3-pentanone

2-Acetamido-5-(3,5-bistrifluoromethylphenyl)-1-(3-indolyl)-4-penten-3-one (0.2 g) was treated in the same manner as Example 4 to yield the title compound as a white solid (190 mg), mp=50°–53° C.; found: C, 58.69; H, 4.27; N, 5.78; $C_{23}H_{20}F_6N_2O_2$ requires C, 58.73; H, 4.29; N, 5.96%.

EXAMPLE 9

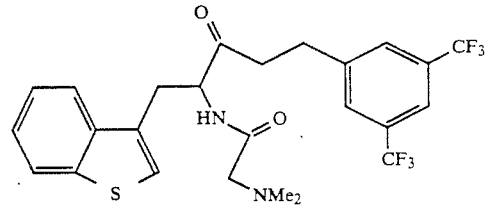

1-(3-Benzo[b]thienyl)-5-(3,5-bistrifluoromethylphenyl)-2-(N,N-dimethylglycinamido)-3-pentanone

(a) 3-(3-Benzo[b]thienyl)-2-t-butyloxycarbonylaminopropionic acid

2-Amino-3-(3-benzo[b]thienyl)propionic acid (*Int. J. Peptide Protein Res.*, (1987), 29, 118) (22.9 g) and sodium carbonate (27.6 g) were added to a mixture of water (350 ml) and 1,4-dioxane (150 ml). Di-t-butyldicarbonate (34.1 g) was added to the mixture and the reaction was stirred for 16 hours and washed with ether (500 ml). The reaction mixture was acidified to pH 3 with solid citric acid and extracted with ethyl acetate to yield the title compound (31.5 g).

(b) Methyl 3-(3-benzo[b]thienyl)-2-t-butyloxycarbonylaminopropionate

The product of Example 9(a) (31.5 g) and Cesium carbonate (15.93 g) were dissolved in methanol and the solvent was removed by evaporation. The residue was dissolved in dimethylformamide and iodomethane (27.8 g) was added. The reaction was stirred for 16 hours then the solvent was removed and the residue partitioned between ethyl acetate and water. The organic extract was washed with sodium bicarbonate solution and water, dried (MgSO4), and evaporated. The residue was purified by column chromatography on silica using ethyl acetate/petroleum ether (1:4) to yield the title compound (27.3 g).

(c) 1-(3-Benzo[b]thienyl)-5-(3,5-bistrifluoromethylphenyl)-2-(t-butyloxycarbonylamino)-3-pentanone Prepared from the product of Example 9(b) using the methods of Examples 1 and 4.

(d)
2-Amino-1-(3-benzo[b]thienyl)-5-(3,5-bistrifluoromethylphenyl)-3-pentanone hydrochloride The product of Example 9(c) was dissolved in methanolic hydrogen chloride and stirred for 16 hours. The solvent was removed under reduced pressure to give the title compound as a white solid.

(e)
1-(3-Benzo[b]thienyl)-5-(3,5-bistrifluoromethylphenyl)-2-(N,N-dimethylglycinamido)-3-pentanone Hydrochloride N,N-Dimethyl glycine (0.206 g) and triethylamine (0.5 g) were dissolved in dry dimethylformamide and cooled to −30° C. before adding isobutylchloroformate (0.27 g). The reaction was stirred for 20 minutes before adding the product of Example 9(d). The reaction was stirred for 1 hour, poured into water and then partitioned between ethyl acetate and water. The organic phase was washed with water (100 ml), sodium bicarbonate solution (100 ml) and water. The organic extract was dried (MgSO$_4$), filtered and evaporated. The residue was purified by column chromatography on silica using ethyl acetate. The resulting oil was treated with ethereal hydrogen chloride and the solid produced after evaporation was crystallised from Et$_2$O/petroleum ether to give the title compound (0.36 g), mp=123°-124° C.; $^1$H NMR (360MHz, D$_6$—DMSO, 300K) δ 9.02 (1H, d, J=7Hz), 7.90-7.87 (5H, m), 7.47-7.36 (3H, m), 4.86-4.79 (1H, m), 3.98-3.79 (2H, m), 3.43-3.38 (1H, m), 3.12-2.97 (5H, m), 2.75 (3H, s), 2.64 (3H, s).

EXAMPLE 10

5-(3,5-Bistrifluoromethylphenyl)-2-t-butyloxycarbonylamino-1-(3-indolyl)-3-pentanone (a) N-Methoxy-N-methyl 2-t-butyloxycarbonylamino-3-(3-indolyl)propionamide N-@-BOC-L-tryptophan (100 g) was dissolved in dimethyl formamide (800 ml) and triethylamine (101 g) was added. The reaction was cooled to −30° C. and isobutyl chloroformate (42.5 ml) was added, maintaining the internal temperature to below −20° C. The reaction was stirred for 15 minutes before adding N,O-dimethyl hydroxylamine hydrochloride (64 g) and then diluting the reaction with dichloromethane (1 l), maintaining the internal temperature below 0° C. The reaction was stirred for 15 minutes, poured into ethyl acetate (3 l) and washed with 10% citric acid (1 l), water (3×1 l), saturated sodium bicarbonate (1 l) and water (1 l). The organic phase was dried (MgSO$_4$), filtered, and evaporated until crystallisation ensued. The suspension was diluted with petroleum ether, filtered and dried to yield the title compound (90.4 g); mp=129°-130° C.; $^1$H NMR (360MHz, D$_6$ DMSO) δ 10.80 (1H, s); 7.51 (1H, d, J=7Hz); 7.33 (1H, d, J=7Hz); 7.16 (1H, s); 7.08-6.97 (3H, m); 4.62-4.58 (1H, m); 3.72 (3H, s); 3.34 (3H, s); 3.02-2.81 (2H, m); 1.31 (9H, s).

b)
2-t-Butyloxycarbonylamino-1-(3-indolyl)-4-dimethylphosphono-3-butanone

Dimethyl methane phosphonate (205 g) was dissolved in tetrahydrofuran (800 ml), cooled to −70° C.; and then treated with n-butyllithium (1.6M in hexane, 900 ml), maintaining the internal temperature of the reaction at below −55° C. The reaction was stirred for one hour before adding the product of part (a) (90 g). The reaction was stirred at −70° C. for 30 minutes before quenching with saturated ammonium chloride. The resulting mixture was extracted with ethyl acetate and the organic extract was washed with water (5×500 ml), dried (MgSO$_4$) and evaporated. The residue was purified on silica (eluting with ethyl acetate) to yield the title compound as an oil (69.0 g); $^1$H NMR (360MHz, CDCl$_3$) δ 10.84 (1H, s), 7.56 (1H, d, J=7Hz), 7.33 (1H, d, J=7Hz), 6.98 (1H, t, J=7Hz), 4.34-4.31 (1H, m), 3.63 (6H, d, J=11Hz), 3.39 (2H, d, J=22Hz), 3.19-3.11 (1H, m), 2.91-2.84 (1H, m); found: C, 55.73, H, 6.34; N, 6.80; C$_{19}$H$_{27}$N$_2$O$_6$P requires C, 55.60; H, 6.63; N, 6.82%.

c)
5-(3,5-Bistrifluoromethylphenyl)-2-t-butyloxycarbonylamino-1-(3-indolyl)-4-penten-3-one Lithium chloride (14.13 g) was dried under vacuum (1 mm, Hg). A solution of the product of part (b) (69.0 g) in acetonitrile (600 ml) was stirred with diisopropylethylamine (43.3 g), and anhydrous lithium chloride (14.13 g) for 30 minutes before adding 3,5-bistrifluoromethylbenzaldehyde (55 g) in acetonitrile (200 ml). The reaction was stirred for two hours then the solvent was removed and the residue partitioned between ethyl acetate and water. The organic phase was washed with 10% citric acid (500 ml), water (500 ml), saturated sodium bicarbonate (500 ml) and water (500 ml). The solution was dried (MgSO$_4$), filtered and evaporated. The residue was purified by column chromatography on silica using ethyl acetate/petroleum ether (1:4) to yield the title compound as a pale yellow solid (77.6 g), mp=137°-138° C.; found: C, 59.23; H, 4.79; N, 5.35; C$_{26}$H$_{24}$F$_6$N$_2$O$_3$ requires C, 59.32; H, 4.60; N 5.32%.

d)
5-(3,5-Bistrifluoromethylphenyl)-2-t-butyloxycarbonylamino-1-(3-indolyl)-3-pentanone The product of part (c) was heated under reflux with tri-n-butyltin hydride (51.12 g) in toluene for 20 hours. The reaction was cooled and purified by column chromatography on silica using ethyl acetate/petroleum ether (1:4) to yield the title compound as a white solid (37.1 g), mp=138°-140° C.; found: C, 59.23; H,4.90; N, 5.28; C$_{26}$H$_{24}$F$_6$N$_2$O$_3$ requires C, 59.09, H, 4.96; N, 5.30%.

EXAMPLE 11

2-Amino-5-(3,5-bistrifluoromethylphenyl)-1-(3-indolyl)-3-pentanone Hydrochloride The compound of Example 10 was treated in a similar manner to Example 9(d) to yield a white solid, mp=84°-86° C.; found: C, 54.40; H, 4.25; N, 6.10; C$_{21}$H$_{18}$F$_6$N$_2$O.HCl requires C, 54.26; H, 4.12; N, 6.03%

EXAMPLE 12

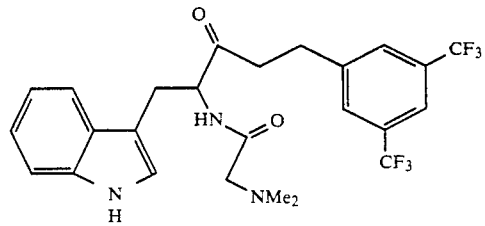

5-(3,5-Bistrifluoromethylphenyl)-2-(N,N-dimethyl-glycinamido)-1-(3-indolyl)-3-pentanone Hydrochloride Prepared from the compound of Example 11 in manner to Example 9(e) to give the title compound as a white solid, mp=194°–196° C.; found: C, 54.11; H, 4.65; N, 7.51; $C_{25}H_{24}F_6N_3O_2 \cdot HCl \cdot 0.25H_2O$ requires C, 54.26; H, 4.64; N, 7.59%.

EXAMPLE 13

2-Benzamido-5-(3,5-bistrifluoromethylphenyl)-1-(3-indolyl)-3-pentanone

The compound of Example 11 (0.55 g) was dissolved in pyridine (10 ml) and benzoyl chloride (0.17 g) was added. The reaction was stirred for 16 hours and then partitioned between 10% citric acid (50 ml) and ethyl acetate (100 ml). The organic phase was washed with water (100 ml) and sodium bicarbonate solution (100 ml), dried (MgSO4) and evaporated to yield an oil which was purified by chromatography on silica using petroleum ether/ethyl acetate (1:3) to yield the title compound as a white solid, mp=119°–122° C.; found: C, 63.28; H, 4.25; N, 5.14; $C_{28}H_{22}F_6N_2O_2$ requires C, 63.16, H, 4.16; N, 5.26%.

EXAMPLE 14

2-Acetamido-1-(3-benzo[b]thienyl)-5-(3,5-bistrifluoromethylphenyl)-3-oximinopentane The compound of Example 4 (0.5 g) was dissolved in methanol followed by hydroxylamine hydrochloride (0.220 g) and sodium acetate (0.7 g). The reaction was stirred for 16 hours, the solvent was removed and the residue was dissolved in ethyl acetate (100 ml), washed with water (100 ml), dried (MgSO4), filtered and evaporated to yield an oil which was purified by chromatography on silica using dichloromethane/Et2O (3:1) to yield the title compound isomer A as a white solid, mp=200°–201° C.; found: C, 54.79; H, 4.24; N, 5.19; $C_{23}H_{20}F_6N_2O_2S$ requires C, 54.98; H, 4.01; N, 5.58%. Further elution yielded the title compound isomer B as a white solid, mp=200°–203° C.; found: C, 55.13; H, 4.14; N, 5.45; $C_{23}H_{20}F_6N_2O_2S$ requires C, 54.98; H, 4.01; N, 5.58%.

EXAMPLE 15

2-Acetamido-5-(3,5-bistrifluoromethylphenyl)-1-(3,4-dichlorophenyl)-3-pentanone a) Diethyl (3,4-Dichlorobenzyl)acetamidomalonate Diethyl acetamidomalonate (48.2 g) was dissolved in ethanol (250 ml) containing sodium ethoxide (10.2 g) and stirred at room temperature for 0.5 hours before adding 3,4-dichlorobenzyl bromide and heating at reflux for 3.5 hours. After cooling, the title compound was collected by filtration and dried under reduced pressure(36.73 g).

b) Ethyl 2-Acetamido-3-(3,4-dichlorophenyl)propionate

The product of part (a) (5 g) was dissolved in ethanol and treated with sodium hydroxide (2N, 6.65 ml). The reaction mixture was stirred for one hour, neutralised with hydrochloric acid and the resulting precipitate was filtered off and dissolved in 1,4 dioxan (50 ml) and heated under reflux for 3 hours. The solvent was evaporated and the residue dissolved in ethyl acetate (500 ml) and washed with sodium bicarbonate (100 ml) and water (100 ml), dried (MgSO4), filtered and evaporated to yield the title compound (3.0 g).

c) 2-Acetamido-5-(3,5-bistrifluoromethylphenyl)-1-(3,4-dichlorophenyl)-3-pentanone The product of part (b) was treated in the same manner as Examples 1 and 4 to yield the title compound as a white solid, mp=124°–126° C.; found: C, 50.35; H, 3.53; N, 2.69; $C_{21}H_{17}Cl_2F_6NO_2$ requires C, 50.42; H, 3.42, N, 2.80%.

EXAMPLE 16

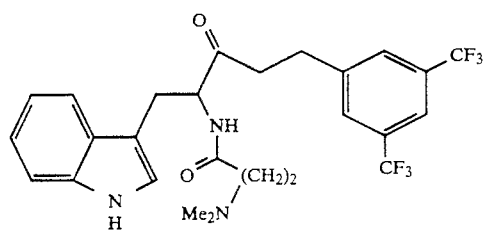

5-(3,5-Bistrifluoromethylphenyl)-2-(3-N,N-dimethylaminopropionamide)-1-(3-indolyl)-3-pentanone Hydrochloride Prepared by the method of Example 12 using 3-N,N-dimethylaminopropionic acid and obtained as a white solid, mp 77°–80° C.; found: C, 55.53; H, 5.26; N, 6.94. $C_{26}H_{30}ClF_6N_3O_3$ requires C, 53.66; H, 5.20; N, 7.22%.

EXAMPLE 17

5-(3,5-Bistrifluoromethylphenyl)-2-(4-(N,N-dimethylamino)butyramido)-1-(3-indolyl)-3-pentanone Hydrochloride Prepared from the compound of Example 11 in a similar manner to Example 9(e) using 4-(N,N-dimethylaminobutyric acid to give the title compound as a white solid, mp 48°–51° C.; Found: C, 54.57; H, 5.38; N, 7.23. $C_{27}H_{29}F_6N_3O_2 \cdot HCl \cdot H_2O$ requires C, 54.41; H, 5.41; N, 7.05%.

EXAMPLE 18

5-(3,5-Bistrifluoromethylphenyl)-2-(5-(N,N-dimethylamino)pentanamido)-1-(3-indolyl)-3-pentanone A solution containing the compound of Example 11 (1.1 g) in dichloromethane (50 ml) was treated with chlorovaleryl chloride (0.52 ml) and triethylamine (0.64 ml) for 16 hours. The reaction was diluted with dichloromethane, washed with dilute hydrochloric acid and aqueous sodium bicarbonate, dried (Na2SO4) and concentrated to give an oil. To a solution containing the forgoing oil in ethanol (5 ml) was added dimethylamine (5 ml of a 33% solution in ethanol) and potassium iodide (50 mg). After stirring for 4 days the mixture was partitioned between ethyl acetate and water. The ethyl acetate solution was separated, dried and concentrated and the residue purified by chromatography on silica gel eluting with ethyl acetate-methanol (95:5) to give the title compound, mp 140° C.; found: C, 59.31; H, 5.47; N, 7.37. $C_{28}H_{31}F_6N_3O \cdot 0.5H_2O$ requires: C, 59.57; H, 5.71; N, 7.44.

EXAMPLE 19

5-(3,5-Bistrifluoromethylphenyl)-2-(cyclopropylcarboxamido)-1-(3-indolyl)-3-pentanone To a solution of 4-bromobutyryl chloride (0.4 g) and triethylamine (0.61 ml) in dichloromethane (20 ml) was added the compound of Example 11 (1.0 g). After stirring for 16 hours the solution was washed with water, dried (Na$_2$SO$_4$) and concentrated. Chromatography on silica gel eluting with ethyl acetate/petroleum ether followed by crystallisation from diethyl ether/petroleum ether gave the title compound, mp 142°–145° C.: found: C, 60.66; H, 4.46; N, 5.59. C$_{25}$H$_{22}$F$_6$N$_2$O$_2$ requires C, 60.48; H, 4.47; N, 5.64.

EXAMPLE 20

5-(3,5-Bistrifluoromethylphenyl)-2-(3-phenylbutyramido)-1-(3-indolyl)-3-pentanone Prepared by the method of Example 20 using phenyl butyric acid and omitting the final lithium hydroxide hydrolysis. Mp 133°–137° C.; found: C, 64.76; H, 4.87; N, 4.72. C$_{31}$H$_{28}$F$_6$N$_2$O$_2$ requires C, 64.80; H, 4.91; N, 4.88.

The following examples illustrate pharmaceutical compositions according to the invention.

EXAMPLE 21A

Tablets Containing 1–25 mg of Compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 21B

Tablets Containing 26–100 mg of Compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 22

Parenteral Injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 23

Topical Formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1-receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 ug of the plasmid DNA into 10 million COS cells was achieved by electroporation in 800 μl of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM N-2-hydroxyethylpiperazine-N'-2-ethane sulphonic acid (HEPES) pH 7.4) at 260 V and 950 μF using the IBI GENEZAPPER (trademark IBI, New Haven, Conn., USA). The cells were incubated in 10% fetal calf serum, 2 mM glutamine, 100 U/ml penicillin-streptomycin, and 90% DMEM media (GIBCO, Grand Island, N.Y., USA) in 5% CO$_2$ at 37° C. for three days before the binding assay.

B. Stable Expression in Chinese Hamster Ovarian Cell Line (CHO)

To establish a stable cell line expressing cloned human NK1R, the cDNA was subcloned into the vector pRcCMV (INVITROGEN). Transfection of 20 μg of the plasmid DNA into CHO cells was achieved by electroporation in 800 μl of transfection buffer supplemented with 0.625 mg/ml Herring sperm DNA at 300 V and 950 μF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans., USA), 0.7 mg/ml G418 (GIBCO)] in 5% CO$_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM MnCl$_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 200 μl of cells were added to a tube containing 20 μl of 1.5 to 2.5 nM of $^{125}$I-SP and 20 μl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was prewetted with 0.1% polyethylenimine. The filter was washed with 3 ml of wash buffer (50 mM Tris pH 7.5, 5 mM MnCl$_2$, 150 mM NaCl) three times and its radioactivity was determined by gamma counter.

The activation of phospholiphase C by NK1R may also be measured in CHO cells expressing the human NK1R by determining the accumulation of inositol monophosphate which is a degradation product of IP$_3$. CHO cells are seeded in 12-well plate at 250,000 cells per well. After incubating in CHO media for 4 days, cells are loaded with 5 μCi of $^3$H-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3 nM to activate the human NK1R. After 30 min of incubation at 37° C., the medium is removed and 0.1N HCl is added. Each well is sonicated at 4° C. and extracted with CHCl$_3$/methanol (1:1). The aqueous phase is applied to a 1 ml Dowex AG 1X8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The data in Table 1 were obtained for compounds of formula (I):

TABLE 1

| SUBSTANCE P ANTAGONISM RESULTS | |
|---|---|
| Compound of Ex # | IC$_{50}$ @ NK1R (nM) |
| 1 | 350 |
| 2 (Isomer A) | 700 |
| 2 (Isomer B) | 300 |
| 3 (Isomer A) | >1 μM |
| 3 (Isomer B) | 350 |
| 4 | 20 |
| 5 (Isomer A) | 190 |
| 5 (Isomer B) | 500 |
| 6 (Isomer A) | 500 |
| 6 (Isomer B) | 30 |
| 7 | 200 |
| 8 | 3 |
| 9 | 30 |
| 10 | 40 |
| 11 | 15 |
| 12 | 10 |
| 13 | 14 |
| 14 (Isomer A) | 200 |
| 14 (Isomer B) | 300 |
| 15 | 40 |
| 16 | 2 |

TABLE 1-continued

| SUBSTANCE P ANTAGONISM RESULTS | |
|---|---|
| Compound of Ex # | IC$_{50}$ @ NK1R (nM) |
| 17 | 0.4 |
| 18 | 0.6 |
| 19 | 2 |
| 20 | 2 |

We claim:
1. A compound of formula (I):

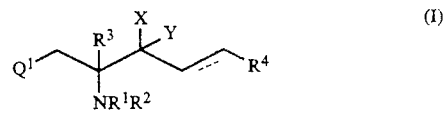

wherein
$Q^1$ is; a heterocyclic group selected from unsubstituted or substituted indolyl, benzothiophenyl and benzofuranyl, said substituents selected from $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are defined below:
the dotted line represents an optional covalent bond;
one of X and Y represents H and the other of X and Y represents hydroxy or $C_{1-6}$alkoxy, or X and Y together form a group =O or =NOR$^5$ where R$^5$ is selected from H and $C_{1-6}$alkyl;
$R^1$ and $R^2$ are each independently selected from H; $C_{1-6}$alkyl optionally substituted by hydroxy, cyano, $COR^c$, $CO_2R^c$, $CONR^cR^d$, or $NR^cR^d$ (where $R^c$ and $R^d$ are each independently selected from H, $C_{1-6}$alkyl and phenyl ($C_{0-4}$alkyl) optionally substituted in the phenyl ring by one or more of $C_{1-6}$alkyl, $C_{1-6}$alkoxy, halo and trifluoromethyl); phenyl ($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $COC_{1-6}$alkylNR$^c$R$^d$; $CONR^cCOOR^d$; and $SO_2R^c$; where $R^c$ and $R^d$ are as above defined;
$R^3$ is selected from H, $C_{1-6}$alkyl and $C_{2-6}$alkenyl; and
$R^4$ is phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ and $CONR^aR^b$, where $R^a$ and $R^b$ are independently selected from H, $C_{1-6}$alkyl, phenyl and trifluoromethyl; or a pharmaceutically acceptable salt thereof.

2. A compound as claimed in claim 1 wherein $R^3$ is selected from H and $C_{1-6}$alkyl.

3. A compound as claimed in claim 1 wherein $R^1$ and $R^2$ are selected from H, $COR^c$ and $COC_{1-6}$alkylNR$^c$R$^d$.

4. A compound as claimed in claim 1 wherein the optional covalent bond is absent.

5. A compound as claimed in claim 1 wherein X and Y together represent =O.

6. A compound as claimed in claim 1 wherein $R^4$ is 3,5-disubstituted phenyl.

7. A compound as claimed in claim 1 wherein $Q^1$ is 3-indolyl.

8. A compound as claimed in claim 1 selected from:
2-acetamido-1-(3-benzo[b]thienyl)-5-(3,5-bistrifluoromethylphenyl)-4-penten-3-one;
2-acetamido-1-(3-benzo[b]thienyl)-5-(3,5-bistrifluoromethylphenyl)-4-penten-3-ol;

2-acetamido-1-(3-benzo[b]thienyl)-5-(3,5-bistrifluoromethylphenyl)-3-methoxy-4-pentene;

2-acetamido-1-(3-benzo[b]thienyl)-5-(3,5-bistrifluoromethylphenyl)-3-pentanone;

2-acetamido-1-(3-benzo[b]thienyl)-5-(3,5-bistrifluoromethylphenyl)-3-pentanol;

2-acetamido-1-(3-benzo[b]thienyl)-5-(3,5-bistrifluoromethylphenyl)-3-methoxypentane;

2-acetamido-5-(3,5-bistrifluoromethylphenyl)-1-(3-indolyl)-4-penten-3-one;

2-acetamido-5-(3,5-bistrifluoromethylphenyl)-1-(3-indolyl)-3-pentanone;

1-(3-benzo[b]thienyl)-5-(3,5-bistrifluoromethylphenyl)-2-(N,N-dimethylglycinamido)-3-pentanone;

5-(3,5-bistrifluoromethylphenyl)-2-t-butyloxycarbonyl amino-1-(3-indolyl)-3-pentanone;

2-amino-5-(3,5-bistrifluoromethylphenyl)-1-(3-indolyl)-3-pentanone;

5-(3,5-bistrifluoromethylphenyl)-2-(N,N-dimethylglycinamido)-1-(3-indolyl)-3-pentanone;

2-benzamido-5-(3,5-bistrifluoromethylphenyl)-1-(3-indolyl)-3-pentanone;

2-acetamido-1-(3-benzo[b]thienyl)-5-(3,5-bistrifluoromethylphenyl)-3-oximinopentane;

5-(3,5-bistrifluoromethylphenyl)-2-(3-N,N-dimethyl aminopropionamido)-1-(3-indolyl)-3-pentanone;

5-(3,5-bistrifluoromethylphenyl)-2-(4-(N,N-dimethyl aminobutyramido)-1-(3-indolyl)-3-pentanone;

5-(3,5-bistrifluoromethylphenyl)-2-(5-(N,N-dimethylamino)pentanamido)-1-(3-indolyl)-3-pentanone;

5-(3,5-bistrifluoromethylphenyl)-2-(cyclopropylcarboxamido)-1-(3-indolyl)-3-pentanone;

5-(3,5-bistrifluoromethylphenyl)-2-(3-phenylbutyramido)-1-(3-indolyl)-3-pentanone;

and pharmaceutically acceptable salts thereof.

9. A pharmaceutical composition comprising a compound as claimed in claim 1 in association with a pharmaceutically acceptable carrier.

10. A method for the treatment of a physiological disorder associated with an excess of tachykinins, which method comprises administration to a patient in need thereof of a tachykinin-reducing amount of a compound according to claim 1.

11. A method according to claim 10 for the treatment of pain or inflammation.

12. A method according to claim 10 for the treatment of migraine.

13. A method according to claim 10 for the treatment of arthritis.

* * * * *